United States Patent [19]
Brinkerhoff et al.

[11] Patent Number: 5,366,478
[45] Date of Patent: Nov. 22, 1994

[54] ENDOSCOPIC SURGICAL SEALING DEVICE

[75] Inventors: Ronald J. Brinkerhoff, New Richmond; Ramesh S. Candadai, Loveland; John A. Cartmill, Cleveland; Jack B. Stubbs, Waynesville, all of Ohio

[73] Assignee: Ethicon, Inc., Somerville, N.J.

[21] Appl. No.: 98,011

[22] Filed: Jul. 27, 1993

[51] Int. Cl.⁵ ............................................. A61B 17/04
[52] U.S. Cl. ..................................... 660/213; 604/256; 604/167; 604/337; 248/56; 49/477.1; 49/475.1
[58] Field of Search .................... 606/213, 215, 93–96, 606/201–203; 604/167, 174, 178, 256, 237; 128/DIG. 26; 248/56; 49/477.1, 475.1; 277/34, 34.3

[56] References Cited

U.S. PATENT DOCUMENTS

| | | | |
|---|---|---|---|
| 2,815,966 | 12/1957 | House | 277/34.3 |
| 3,038,732 | 6/1962 | Scott et al. | 277/34.3 |
| 3,480,017 | 11/1969 | Shute | 606/193 |
| 3,970,089 | 7/1976 | Saice | 277/34.3 X |
| 4,241,735 | 12/1980 | Chernov | 604/337 X |
| 5,167,637 | 12/1992 | Okada et al. | 604/167 |
| 5,192,301 | 3/1993 | Kamiya et al. | 606/213 |
| 5,211,633 | 5/1993 | Stouder, Jr. | 604/167 |

*Primary Examiner*—Peter A. Aschenbrenner
*Attorney, Agent, or Firm*—Matthew S. Goodwin

[57] ABSTRACT

A sealing device for endoscopic surgical procedures is disclosed. In one embodiment, the device has two inflatable toroidal sections connected by a transition section. The device is partially inserted into an abdominal opening in a deflated state, and then inflated to provide a seal for obstructing the passage of gas from the abdominal cavity during endoscopic surgery. Endoscopic instruments, or alternatively, the surgeon's hand, can penetrate through the lumen of the toroidal sections of the device. The lumen then conforms to the shape of the instrument or hand passed through it to maintain an adequate seal.

In another embodiment, a sealing device to seal a trocar is disclosed. The device is an inflatable toroid shaped to fit securely within the housing of the trocar. Means are provided to selectively inflate or deflate the device to perform its intended sealing function, and instruments can be passed through the lumen of the toroid to access the surgical site without destroying the integrity of the seal.

5 Claims, 6 Drawing Sheets

ENDOSCOPIC SURGICAL SEALING DEVICE

FIELD OF INVENTION

This invention relates to the field of surgical devices. More particularly, it relates to such a device for providing a seal during endoscopic surgery.

BACKGROUND OF THE INVENTION

In the practice of abdominal surgery, which requires the examination and manipulation of intraperitoneal and extraperitoneal organs and tissues, surgeons most often employ a long established technique of opening the abdominal wall with an incision large enough to accommodate instruments required, as well as the surgeon's hands, and to allow procedures such as anastomosis or removal of diseased organs or portions thereof. The advantages of this technique include a large degree of freedom of motion for successfully completing the procedure, sufficient space for mechanical leverage which may be necessary, and above all, tactile feedback response to the surgeon when using his hands to feel the texture, temperature, and physical response of the tissues. The disadvantages of this traditional technique, however, include long healing and recuperative time with considerable post-operative pain, and adhesion formation which can cause pain and bowel obstruction. Additionally, the traditional technique may increase the complexity of later surgery, as well as increase the possibility of post-operative morbidity and unsightly scars remaining after the procedure is completed.

In order to overcome the disadvantages of the traditional abdominal surgery method using a large incision, laparoscopic techniques have been developed which use several smaller puncture openings in the abdominal wall. These openings are used to inflate the abdominal cavity with a gas to elevate the abdominal wall away from the organs, and to allow room for the manipulation of the organs. The openings also provide means to introduce light generating and optical viewing instruments to observe the abdominal cavity, and to manipulate the organs in order to accomplish the desired results. This laparoscopic technique is becoming widely accepted because of its many advantages. These advantages include reduced adhesions, shorter recovery time, and less post-operative pain. There are also some disadvantages. For example, there are limitations on freedom to manipulate organs, and the surgeon's viewing ability, although magnified with the aid of a laparoscope, lacks depth perception. Most importantly, there is a lack of tactile feedback of the tissue through the surgeon's hands. Also, when a tissue specimen must be removed, a larger opening must be made in the abdominal wall near the end of the procedure, causing loss of gas pressure, collapse of the abdominal wall, and loss of interior working and viewing space.

The laparoscopic technique uses smaller puncture openings in the abdominal wall as described. These openings are usually made with a puncture device called a trocar. The trocar point and attached shaft are usually contained in a hollow circular tube which remains in the abdominal wall after puncture and through which other instrument shafts are passed to be used in the operating procedure. A sealing feature must be included in the trocar cannula body in order to maintain the gas pressure as described above. Various sizes and shapes of instruments are used in these procedures and sealing between the instruments and the trocar body must be achieved. Also, internal sealing is required within the instrument body passing through the cannula to avoid gas leakage. The importance of these sealing requirements is indicated by their inclusion in endoscopic instrument patents. For example, U.S. Pat. Nos. 5,104,383 and 5,197,955, describe sealing mechanisms between trocars and instruments passed through them. Also, the endoscopic instruments themselves contain internal sealing means to reduce the loss of gas pressure in the abdominal cavity. U.S. Pat. Nos. 5,100,420 and 5,171,249, describe internal sealing means in endoscopic instruments.

Combining the advantages of the traditional and the laparoscopic techniques for abdominal surgery is the laparoscopic assisted procedure. In this procedure, the normal laparoscopic small puncture openings are made with the exception that one opening is made late in the procedure and large enough to allow a surgeon's hand to pass through the abdominal wall in order to remove tissue or deliver a mobile organ for surgery. When this larger opening is made, gas pressure is lost and the procedure must be completed by using a plug usually made of gauze to seal the opening to allow reinflation. This sequence of: removing the plug, losing gas pressure, performing a surgical step, replugging the opening, and reinflating the abdominal cavity can be repeated several times before the surgical procedure is completed.

Accordingly, it is an object of the present invention to allow the advantages of the laparoscopic method of maintaining gas pressure in the abdominal cavity, and of requiring relatively small incisions for quicker recovery than the traditional method, yet allows the surgeon the important feature of tactile feedback to determine directly the information needed to successfully conclude the procedure as well as allow removal of the specimen.

In addition, it is an object to provide a unique gas pressure sealing means that can be used to seal between an abdominal wall opening and a surgeon's hand in addition to a sealing means that can be used in a trocar device to seal between the trocar housing and any instrument which can pass through the trocar tube.

Another object of the present invention is to seal the abdominal cavity or trocar device when nothing is placed through the sealing device in order to maintain gas pressure in the abdominal cavity.

Furthermore, another object of the present invention is to provide a sealing means between the trocar cannula and the different instruments which are passed through the trocar cannula for use during the operating procedure as well as maintaining gas pressure when no instruments are inserted in the trocar cannula.

SUMMARY OF THE INVENTION

According to the present invention, the object of providing and maintaining gas pressure during any laparoscopic, and more particularly, laparoscopic assisted procedure is achieved by an inflatable sealing device for the abdominal wall. The device has an overall toroidal shape comprising first and second inflatable toroidal segments positioned outside and inside the abdominal cavity, respectively. These segments are connected by a transition section. The center opening of the toroidal shape of the device, which characterizes the device, is closed to seal the inflated abdomen when the device is inflated. The sealing device has inflation means for selectively inflating or deflating the device, either manually or automatically. An additional feature of the present invention is that gas pressure is maintained while either an instrument or the surgeon's hand is passed through the sealing device.

Another feature is that the device can be built in any size needed to accommodate the surgeon's hand, instrument dimension, or specimen to be removed.

According to another advantageous feature of the present invention, the sealing device can be used inside an endoscopic puncturing instrument, such as a trocar, to allow a simpler device for sealing from loss of gas pressure when passing instruments into and out of the trocar, or when no instruments are in place in the trocar cannula.

An additional feature of the present invention in the preferred embodiment, is that the device further comprises stiffening means, such as a flexible stiffening ring on either or both of the first and second inflatable segments of the seal device to give it more stability in order to insert and properly position the second segment into the abdominal cavity when desired, as well as positioning the first segment outside of the abdominal cavity to support instruments during the procedure.

Another advantage of the present invention is that the seal device can be made using commercially available biocompatible latex, natural rubber, or polymeric materials.

In yet another advantage of the present invention, the device can be made utilizing current manufacturing technology for inflatable structures.

The sealing device of this invention can be used during any surgical procedure requiring the insufflation of the abdominal cavity during surgery, particularly laparoscopic assisted surgical procedures.

BRIEF DESCRIPTION OF THE DRAWINGS

·An embodiment of the invention is described by way of example with reference to the accompanying drawings, in which.

DETAILED DESCRIPTION OF THE PREFERRED EMBODIMENTS

For the purpose of defining this invention, the term "toroidal" as it is used to describe the shape of the sealing device refers not only to the classical toroid having a substantially circular cross-section, but also to any other desirable shape with a different cross-sectional configuration, provided such other shape has a central lumen which is characteristic of the classical toroid. For example, it is within the scope of the claimed invention for any of the toroidal sections described in the specification to have a cross-sectional shape which is square, triangular, or the like.

FIGS. 1-4 show a preferred embodiment of an inflatable sealing device used in a laparoscopic assisted operating procedure to maintain internal inflation pressure in the abdominal cavity while allowing either the surgeon's hand or an endoscopic instrument to pass through the device.

Figure 5:
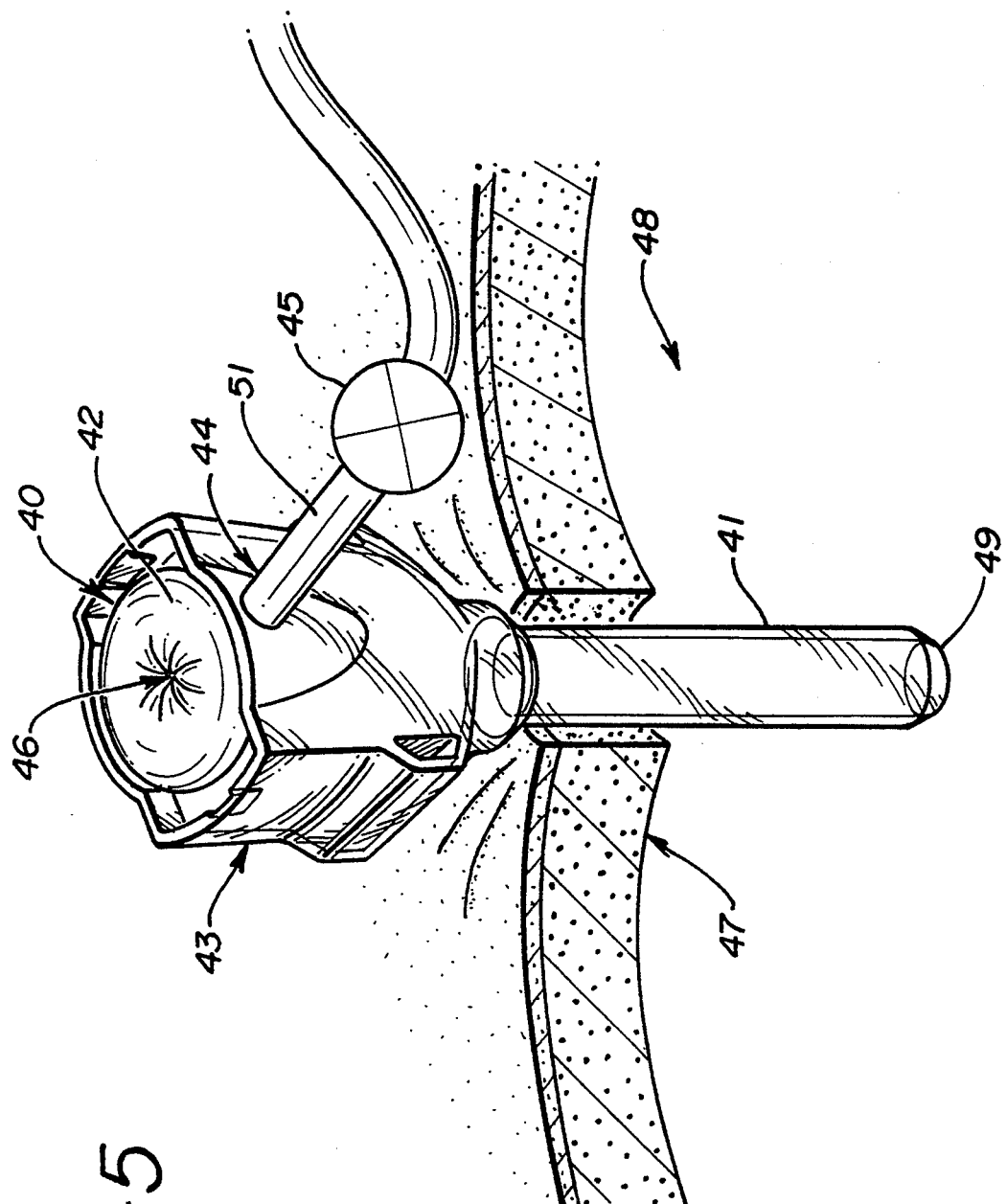
FIG. 5 is a diagrammatic view of another preferred sealing device for use in an endoscopic puncturing instrument, such as a trocar.
Figure 6:
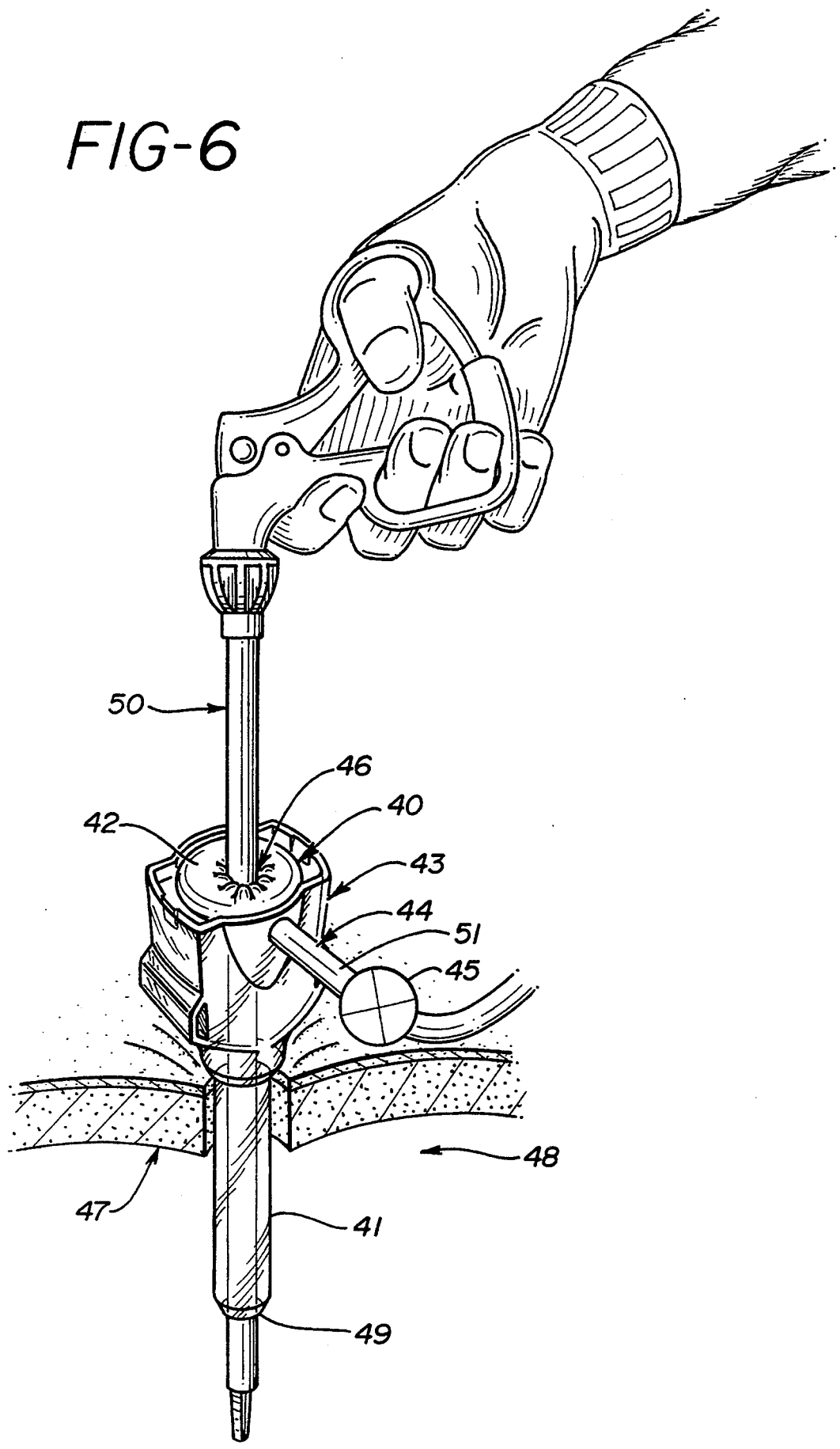
FIG. 6 is a view of the same device as shown in FIG. 5 with an endoscopic manipulation instrument inserted through it.

FIGS. 5 and 6 show another preferred embodiment of an inflatable sealing device used in a trocar instrument to provide a seal around an endoscopic instrument inserted through it and thereby maintain pressure in the abdominal cavity.

In one of the preferred embodiments, as shown at FIGS. 1 through 4, the endoscopic surgical sealing device 10 has a first inflatable toroidal section 11 for positioning outside of the abdominal wall 12, a second toroidal section 13 for positioning inside the body cavity 14 and a transition section 15, which communicates with the first and second inflatable toroidal sections. An inflation means 16 for inflating and deflating the device is attached to the first inflatable section 11. The inflation means 16 includes a tubular conduit 17 which contains a valve 18 shown schematically to selectively inflate or deflate the sealing device 10. Such valves are commonly used in the medical device field and are known to someone skilled in the art.

The first inflatable toroidal section 11 contains flexible stiffening rings 19, and the second toroidal section 13 includes similar flexible stiffening rings 20 attached to the sealing device. These stiffening rings 19 and 20 preferably encircle the circumference of the first and second sections, and therefore provide shape when the sealing device is deflated as illustrated at FIG. 1, as well as facilitate insertion of the device into the body cavity 14.

Figure 1:
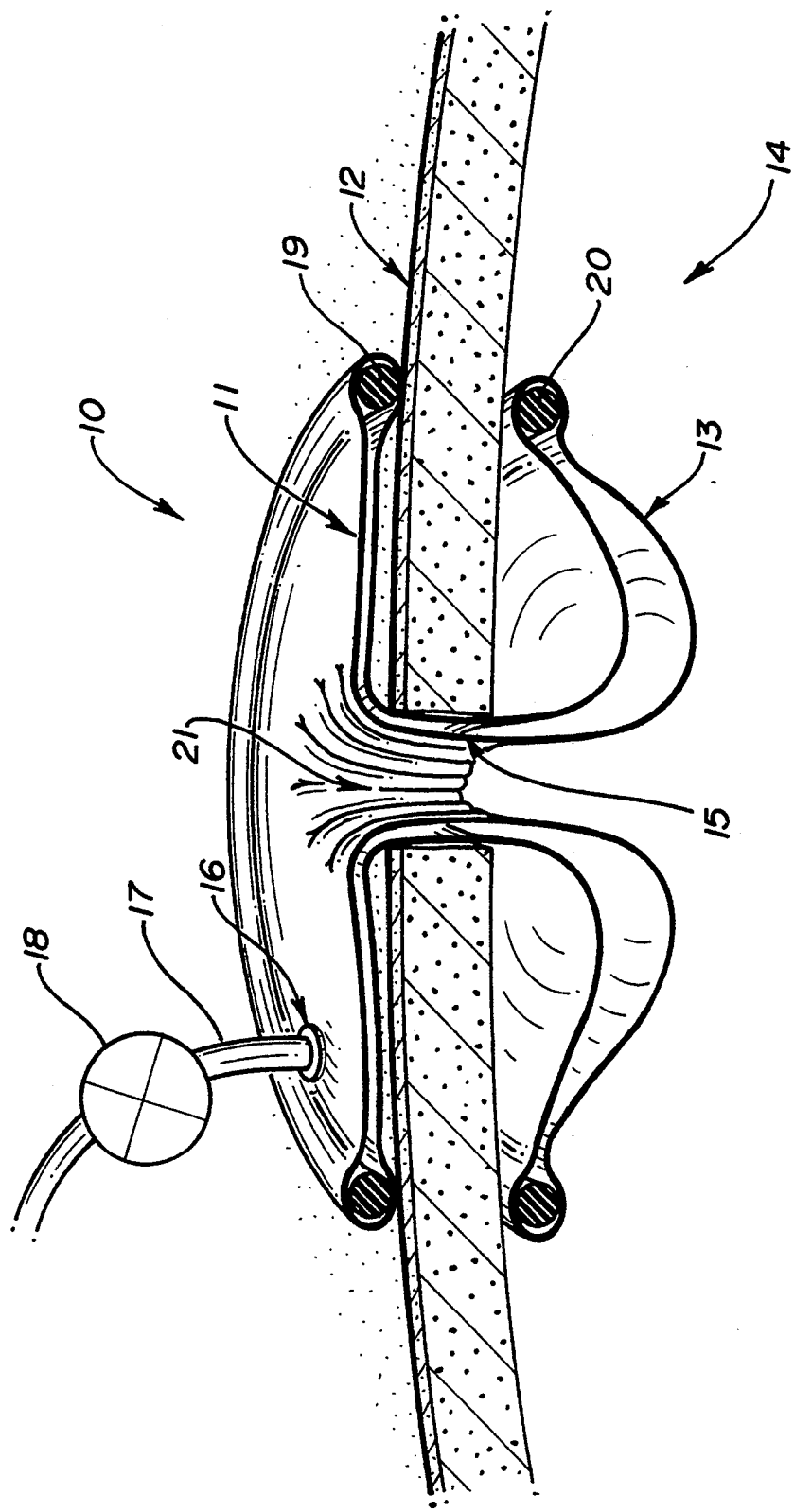
FIG. 1 is a diagrammatic sectional view of a preferred sealing device in its deflated state but positioned in the abdominal cavity.
Figure 2:
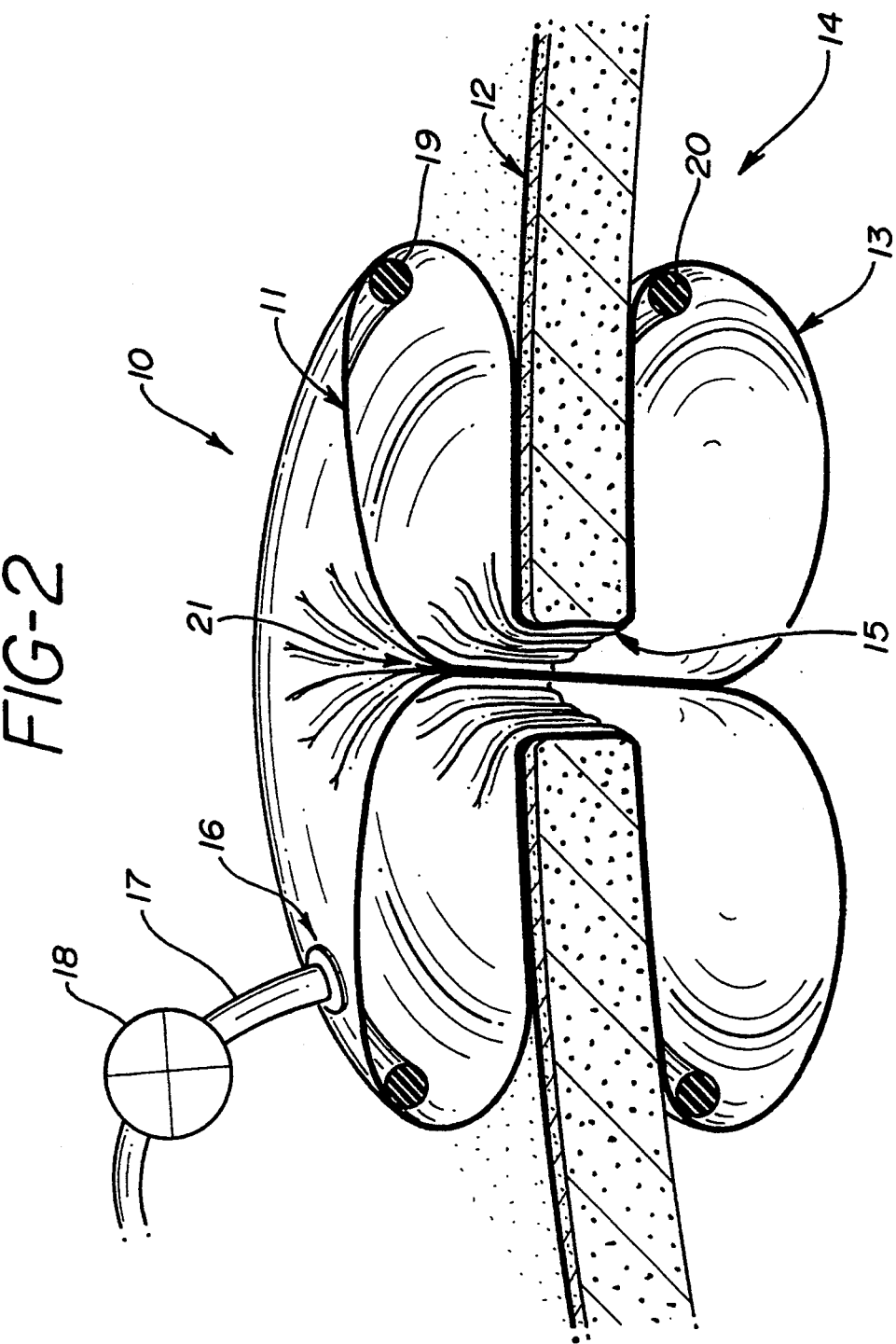
FIG. 2 is a view of the same device in the inflated state functioning as a sealing device.

The function of the endoscopic sealing device is illustrated at FIGS. 1 and 2. When the sealing device 10 is deflated, it is inserted into the body cavity 14 as shown at FIG. 1. In its position shown at FIG. 1, the central lumen 21 of the device is open and the body cavity 14 is not sealed. FIG. 2 shows the sealing device 10 inflated, and consequently the central lumen 21 is closed causing the body cavity 14 to be sealed against leakage of gas.

Figure 3:
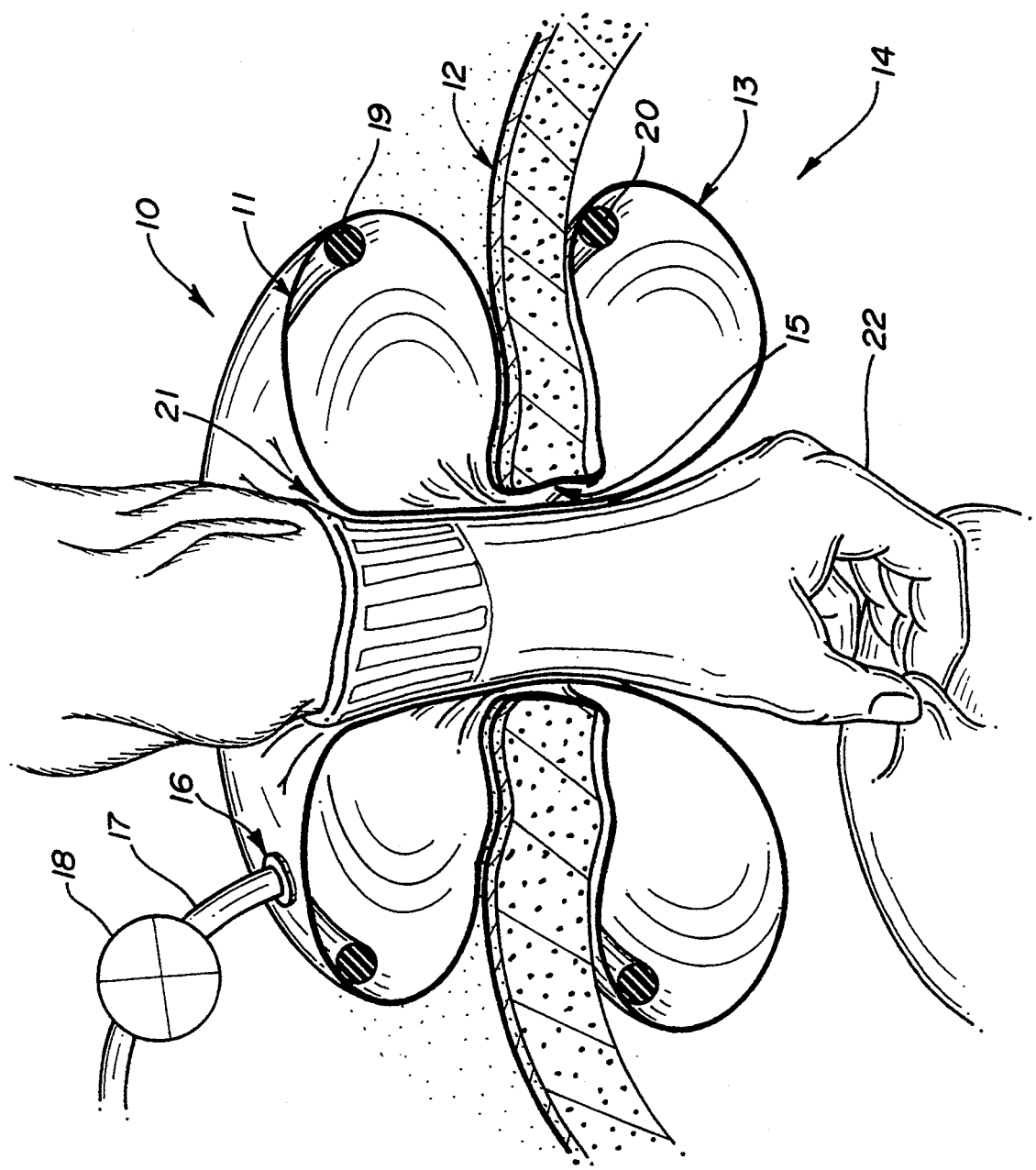
FIG. 3 is a diagrammatic sectional view of the sealing device with the surgeon's hand inserted through the device.

FIG. 3 shows the sealing function of the sealing device 10 when the surgeon's hand 22 is positioned inside the body cavity 14. The central lumen 21 is easily opened to allow the surgeon's hand 22 to be inserted inside the body cavity 14. Once the surgeon's hand 22 is inserted through the central lumen 21, the lumen 21 conforms to the shape of the surgeon's hand because of the compliant nature of the sealing device 10 when the first and second sections of the device are inflated. Therefore, a gaseous seal capable of maintaining a substantially constant pressure in the abdominal cavity can be achieved. When the surgeon's hand 22 is withdrawn from the central lumen 21 of the sealing device 10, the central lumen 21 closes upon itself as shown at FIG. 2, and thus continues to function to seal the abdominal wall 12.

Figure 4:
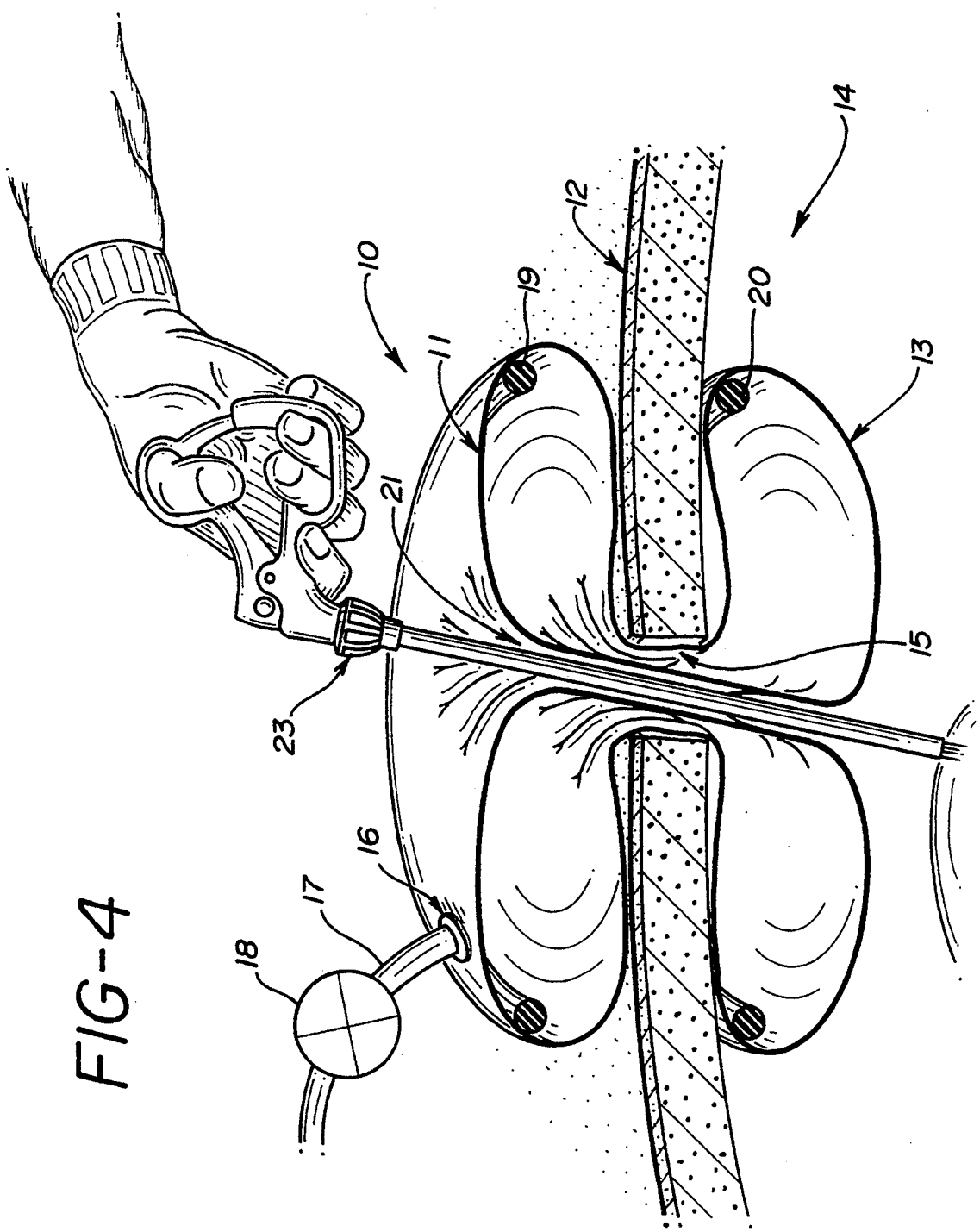
FIG. 4 is a view of the same device with an endoscopic manipulation instrument inserted through the device.

Likewise, FIG. 4 illustrates the sealing function of the endoscopic sealing device 10 when an endoscopic instrument 23 is positioned through the central lumen 21 of the sealing device 10. The internal gas pressure forces the central lumen 21 to close around the surface of the endoscopic instrument 23 to seal the abdominal cavity 14 from gas leakage. When the endoscopic instrument 23 is withdrawn from the sealing device 10, the central lumen 21 again closes upon itself as shown at FIG. 2 and continues to function to seal the opening in the abdominal wall 12.

The inflatable endoscopic sealing device 10 is preferably made of one piece, but could be made in the form of pieces that are initially separate and then assembled by techniques known to persons skilled in the art.

The flexible stiffening rings 19 and 20 in the first and second toroidal sections 11 and 13, respectively, are preferably attached to the sealing device 10 using a flexible adhesive or heat sealing method. The rings are preferably attached to the internal surface of the sealing device 10 which is exposed to the internal gas pressure in the device 10 when the device is inflated. This embodiment has the advantage of smooth surface appearance when viewed from the surgeon's standpoint. Alternatively, the stiffening rings 19, 20 can be attached on the surface which is not exposed to internal gas pressure.

The overall dimensions of the endoscopic sealing device 10, when inflated, include a minimum outside diameter of about 4 to 6 inches, and an approximate overall height of about 4 to 8 inches. The approximate height of the inflated first toroidal section 11 should be at least 2 inches to safely support an endoscopic instrument when the surgeon is not handling the instrument, and the maximum height of the second toroidal section 13 should be about 2 inches so that the sealing function is assured and the resulting volume does not interfere with the functioning of the endoscopic instrument inside the body cavity 14. The transition section 15 should have a minimum height dimension of 1-2 inches to accommodate the thickness range of the abdominal wall 12 of most patients.

The sealing device 10 is preferably composed of a biocompatable latex or polymer such as polyethylene, polypropylene, or polyamide. The material should be capable of being inflated and deflated numerous times without losing its originally formed shape, conform to the instrument 23 or surgeon's gloved hand 22 when inflated, and return to its original deflated shape as shown in FIG. 1.

The inflation pressure for the endoscopic sealing device 10 should be at a minimum value greater than the normal range of gas pressure used in the abdominal cavity 14, which usually ranges from 8 to 15 mm mercury (0.14 to 0.28 psi).

Another embodiment of the endoscopic sealing device is shown at FIGS. 5 and 6. In this embodiment, the inflatable sealing device 40 is shown as used in a trocar 41. The trocar application would require one inflatable toroidal section 42 inserted and attached to a trocar housing 43. The sealing device 40 has an inflation and deflation means 44 which includes a tubular conduit 51 containing valve 45 shown schematically in FIGS. 5, 6 to selectively inflate or deflate the sealing device 40.

The function of the sealing device in this embodiment is illustrated in FIGS. 5 and 6. In the laparoscopic procedure, the trocar 41 is inserted through the abdominal wall 47 into the abdominal cavity 48 to allow instruments to pass through the abdominal wall 47 to accomplish the procedure while the abdominal cavity 48 is under gas pressure. The trocar 41 is naturally sealed at the abdominal wall 47 by the elastic nature of the tissue in the abdominal wall 47. The trocar opening 49 into the body cavity 48 is sealed against leakage of gas by the closing of the central lumen 46 of the sealing device 40 when the sealing device 40 is inflated as illustrated in FIG. 5. The central lumen 46 of the sealing device 40 is easily opened by inserting an endoscopic instrument 50. The gas sealing is accomplished between the endoscopic instrument 50 and the trocar 41 as shown in FIG. 6 by inflation pressure inside the toroidal section 42 of the sealing device 40 forcing the central lumen 46 to close tightly around the movable endoscopic instrument 50.

The inflatable endoscopic sealing device 40 is preferably made of one piece, but could be made in the form of pieces that are initially separate and then assembled by techniques known to persons skilled in the art. The endoscopic sealing device 40 is attached to the trocar housing 43 using a flexible adhesive. Such adhesives are known to those skilled in the art.

The overall dimensions for the sealing device 40 will be determined by the size of the trocar housing 43 to which the sealing device 40 is attached. A typical trocar housing 43 would require the sealing device to have an outside diameter of approximately two inches in the deflated state and height of the toroidal section 42 of approximately 1-2 inches in the inflated state of the sealing device 40.

The inflation pressure of this embodiment of the sealing device 40, and its material of construction, are generally the same as those specified for the embodiment of the sealing device shown in FIGS. 1 to 4.

Although this invention has been specifically described with respect to the preferred embodiments, numerous additional embodiments feasible to those skilled in the art are well within the spirit and scope of the invention as defined by the claims set forth below.

What is claimed is:

1. An endoscopic surgical sealing device for maintaining gas pressure within an inflated abdominal cavity during endoscopic surgery; said device comprising:
   a first inflatable toroidal section for positioning outside the abdominal cavity;
   a second inflatable toroidal section for positioning inside the abdominal cavity;
   a transitional section communicating with said first and second inflatable sections;
   said first and second inflatable toroidal sections and said transitional section defining a continuous lumen providing a passageway from the outside of the abdominal cavity to the inside of the abdominal cavity; and,
   inflation means attached to said first inflatable section for selectively:
   a) inflating said first and second inflatable sections so as to close said lumen and prevent pressurized gas from escaping the abdominal cavity, or
   b) deflating said first and second inflatable sections.

2. A surgical sealing device according to claim 1, wherein said device further comprises stiffening means mounted within said first and second sections for facilitating the handling of said device.

3. A surgical sealing device according to claim 2, wherein said stiffening means are flexible rings.

4. A surgical sealing device according to claim 2, wherein said device is composed of a material selected from the group consisting of a biocompatible latex and a polymer.

5. A surgical sealing device according to claim 4, wherein said polymer is selected from the group consisting of polyethylene, polypropylene, and polyamide.

* * * * *